(12) United States Patent
Schlichte et al.

(10) Patent No.: US 8,632,666 B2
(45) Date of Patent: Jan. 21, 2014

(54) EXPLOSION-PROOF SENSOR

(75) Inventors: Mladen Schlichte, Lübeck (DE); Björn Lange, Teschow (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 346 days.

(21) Appl. No.: 12/881,539

(22) Filed: Sep. 14, 2010

(65) Prior Publication Data
US 2011/0094880 A1 Apr. 28, 2011

(30) Foreign Application Priority Data
Oct. 28, 2009 (DE) .......................... 10 2009 051 072

(51) Int. Cl.
*G01N 27/407* (2006.01)
*G01N 27/403* (2006.01)
(52) U.S. Cl.
USPC ............................................. 204/424; 422/98
(58) Field of Classification Search
USPC ..................... 204/400, 421–429, 431; 422/98
See application file for complete search history.

(56) References Cited

U.S. PATENT DOCUMENTS

| 4,596,975 | A | | 6/1986 | Reddy et al. |
| 5,601,693 | A | * | 2/1997 | Davies .......................... 204/400 |
| 6,469,303 | B1 | * | 10/2002 | Sun et al. ...................... 250/343 |
| 6,607,642 | B1 | * | 8/2003 | Kiesele et al. ................ 204/415 |
| 2005/0217370 | A1 | | 10/2005 | Takahashi et al. |
| 2006/0243029 | A1 | * | 11/2006 | Lange et al. ................. 73/31.05 |
| 2008/0092628 | A1 | * | 4/2008 | Oishi et al. ................... 73/25.01 |

FOREIGN PATENT DOCUMENTS

| DE | 32 04 279 A1 | 8/1983 |
| DE | 102005020131 | 5/2006 |
| EP | 0 094 863 | 11/1983 |
| EP | 2 093 846 A1 | 8/2009 |
| GB | 2068561 A | 8/1981 |
| GB | 2332525 A | 6/1999 |
| GB | 2425605 A | 11/2006 |
| WO | WO 2004/048955 A2 | 6/2004 |

\* cited by examiner

*Primary Examiner* — Alex Noguerola
(74) *Attorney, Agent, or Firm* — McGlew and Tuttle, P.C.

(57) ABSTRACT

An explosion-proof sensor for detecting combustible gases is provided with a glass seal (9) for establishing an electrically conductive connection with the interior of the housing. The sensor is improved in terms of the pressure resistance of the housing. The glass seal (9) has a bending-resistant casting compound (16, 17, 18) mechanically stabilizing the glass seal (9) on at least one side.

20 Claims, 2 Drawing Sheets

EXPLOSION-PROOF SENSOR

CROSS REFERENCE TO RELATED APPLICATIONS

This application claims the benefit of priority under 35 U.S.C. §119 of German Patent Application DE 10 2009 051 072.9 filed Oct. 28, 2009, the entire contents of which are incorporated herein by reference.

FIELD OF THE INVENTION

The present invention pertains to an explosion-proof sensor, e.g., for detecting combustible/toxic gases or smoke.

BACKGROUND OF THE INVENTION

For example, gas sensors, which contain a catalyst, which is heated to a predetermined temperature, as a result of which the combustible gases are catalytically burnt on the surface of the sensor while consuming part of the oxygen present in the gas being measured and raise the temperature in the process, are used to detect combustible/toxic gases. The rise in the sensor temperature occurring during the combustion reaction is analyzed as a measured signal for the concentration of the gas in the air mixture to be analyzed.

To carry out the measurement, a catalytically active sensor element and a passive sensor as a compensator are usually arranged in one half of a bridge, the passive sensor being used to compensate the ambient temperature effect. The detuning of the bridge is an indicator of the catalytic conversion of the combustible gas component at the catalytically active sensor element.

To suppress inflammation of the combustible gas, at least the catalytically active sensor element is accommodated in a sensor housing, which is covered, for example, with a porous, gas-permeable sintered material as a flame trap.

A catalytically active gas sensor of this type is known from EP 94 863 A1. The catalytically active sensor element is located in a sensor housing, which housing is delimited by a porous, gas-permeable sintered material. Two metal pins, which contact the sensor element, are led through a glass pane on the underside of the sensor housing to the outside. The sensor element is surrounded by zeolite material in order to reduce the energy consumption due to the insulating action and adsorption properties of that material and to prolong the service life.

The prior-art glass seal for the metal pins is not suitable for use in explosion-proof sensor housings encapsulated in a pressure-proof manner. Such sensor housings must be dimensioned such that they withstand 1.5 to 4 times the pressure that can build up in the interior of the sensor housing in case of an explosion. Even a pressure resistance of up to and above 400 bar is required in pertinent standards. A flat pane of glass material, i.e., a glass pane with a small thickness to diameter ratio, which is weakened, moreover, by the integration of a plurality of metal pins, is destroyed by cracking in case of exposure to the pressure emanating during a gas explosion.

Pressure-proof encapsulated sensors which comprise a metal housing, which is embedded in a plastic material, are known as well. Certain minimum casting thicknesses must be maintained in such housing designs and compliance with certain standard requirements must be demonstrated. A sensor in a plastic housing appears, for example, from WO 2004/048955 A1.

A gas sensor, in which the metal pins contacting the sensor element are fused each individually into separate glass inserts in the bottom plate of the sensor housing, is known from DE 10 2005 020 131 B3. Even though the prior-art gas sensor has a high pressure resistance due to the glass inserts arranged individually, the manufacturing process is relatively complicated. A separate hole must be prepared for each metal pin in the bottom plate. The metal pins must be placed very exactly centrally in their holes because of the small hole diameters necessary to achieve the pressure resistance in order to prevent an electric short-circuit between the metal pin and the bottom plate. In addition, specially selected glass/metal pairs and/or sealing oxide layers are necessary because of the thermal expansion and a minimum thickness of the bottom plate and glass inserts is necessary for the purpose of mechanical stability.

SUMMARY OF THE INVENTION

The basic object of the present invention is to propose a sensor with a simplified housing design for a pressure-proof encapsulation.

According to the invention, an explosion-proof sensor is provided with a sensor element, which is connected in an electrically conductive manner to metal pins. The sensor includes a sensor housing enclosing the sensor elements on all sides and with at least one glass seal for the one or more metal pins. The glass seal has a bending-resistant casting compound supporting the glass seal at least on one side.

The glass seal may have a one-piece glass insert, in which the metal pins are accommodated.

The bending-resistant casting compound may be a first casting compound provided on the sensor outside of the glass seal. A second casting compound may be arranged on the sensor inside of the glass seal. Advantageously the casting compound may be present on both sides of the glass seal.

Cements, ceramic compounds, epoxy resins or polyurethanes may be provided as the casting materials. The casting compound may consist of a plurality of layers. The casting compound may be a polyurethane or epoxy resin in the area of current or voltage-carrying elements.

The sensor is advantageously intended for measuring combustible or toxic gases or for detecting smoke.

The advantage of the explosion-proof sensor proposed according to the present invention can be seen in that a glass seal, which is not pressure-proof per se, is mechanically stabilized by the application of a bending-resistant casting compound and cracking or even a complete pushing out of the glass insert is prevented as a result. Based on the mechanical stabilization by the casting compound, it is possible to use both glass seals with a single, large glass insert for many metal pins and glass seals without sealing oxide layers or with glass-metal pairs with coefficients of thermal expansion that are coordinated less closely with one another. Another advantage of the explosion-proof sensor according to the present invention can be seen in that the casting compound can serve other, desired purposes in addition to the mechanical stabilization of the glass seal. Among other things, the electric insulation of the conductive contacts, which is at times also required by the pertinent standards, creep resistance, protection of the metal pins against bending and strain relief of the cables soldered to the metal pins, may be mentioned here. To serve a combination of the above-mentioned purposes at the same time, it may be meaningful to combine a multilayer casting compound of casting materials possessing different properties. For example, ceramics and cements are well suited for mechanical stabilization on account of their high bending resistance, while polyurethanes and epoxy resins have advantages in terms of insulation strength and adhesion/pull relief.

The casting compound may be provided on one side or both sides of the glass seal. For mechanical stabilization, it is preferably on the side of the glass seal facing away from the pressure. A bilateral casting compound is meaningful, e.g., in cases in which a possible pressure load must be assumed to occur from both sides.

The thickness of the casting compound depends on the volume and the diameter of the sensor housing and the dimensions of the glass seal within the sensor housing and is typically in a range of 3 mm to 25 mm.

Cements, ceramic casting compounds, epoxy resins and polyurethanes are suitable for use as casting materials.

In case of a one-sided, single-layer casting compound with epoxy resin or cement, typical thicknesses of the casting compound are about 3 mm in case of a sensor housing volume smaller than 10 $cm^3$, whereas the thickness of the casting compound equals about 6 mm in case of a sensor housing volume between 10 $cm^3$ and 100 $cm^3$. The thickness of the casting compound is about 10 mm in case of a sensor housing volume larger than 100 $cm^3$. However, depending on the desired approval and the standard applied, casting compound heights of up to 25 mm and greater may be meaningful as well. The diameter of the casting compound is typically in a range of 3 mm to 100 mm.

To better anchor the casting compound in the sensor housing, the sensor housing may be provided with an undercut or an internal thread to ensure that the casting compound is in contact with both the glass seal and parts of the sensor housing in a positive-locking manner. The glass insert of the glass seal is typically accommodated in a metallic bottom plate, said bottom plate being welded to the sensor housing.

The modulus of elasticity of the casting compound is typically in a range of 50 $kN/mm^2$ to 150 $kN/mm^2$ for ceramic casting compounds. The modulus of elasticity may reach up to 380 $kN/mm^2$ for high-purity ceramic casting compounds. Suitable materials are silicon carbide, silicon nitride, alumina, zirconium oxide, aluminum nitride or borosilicate glass. The modulus of elasticity for casting compounds based on plastics is preferably in a range of 1 to 100 $N/mm^2$ for silicones and polyurethanes and 1 to 10 $kN/mm^2$ for—possibly filled—epoxy resins. The scope of protection of the device according to the present invention is not limited by the fact that certain materials for the casting compound are named, because casting materials that possess material properties similar to those of the materials already mentioned are comprised as well.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
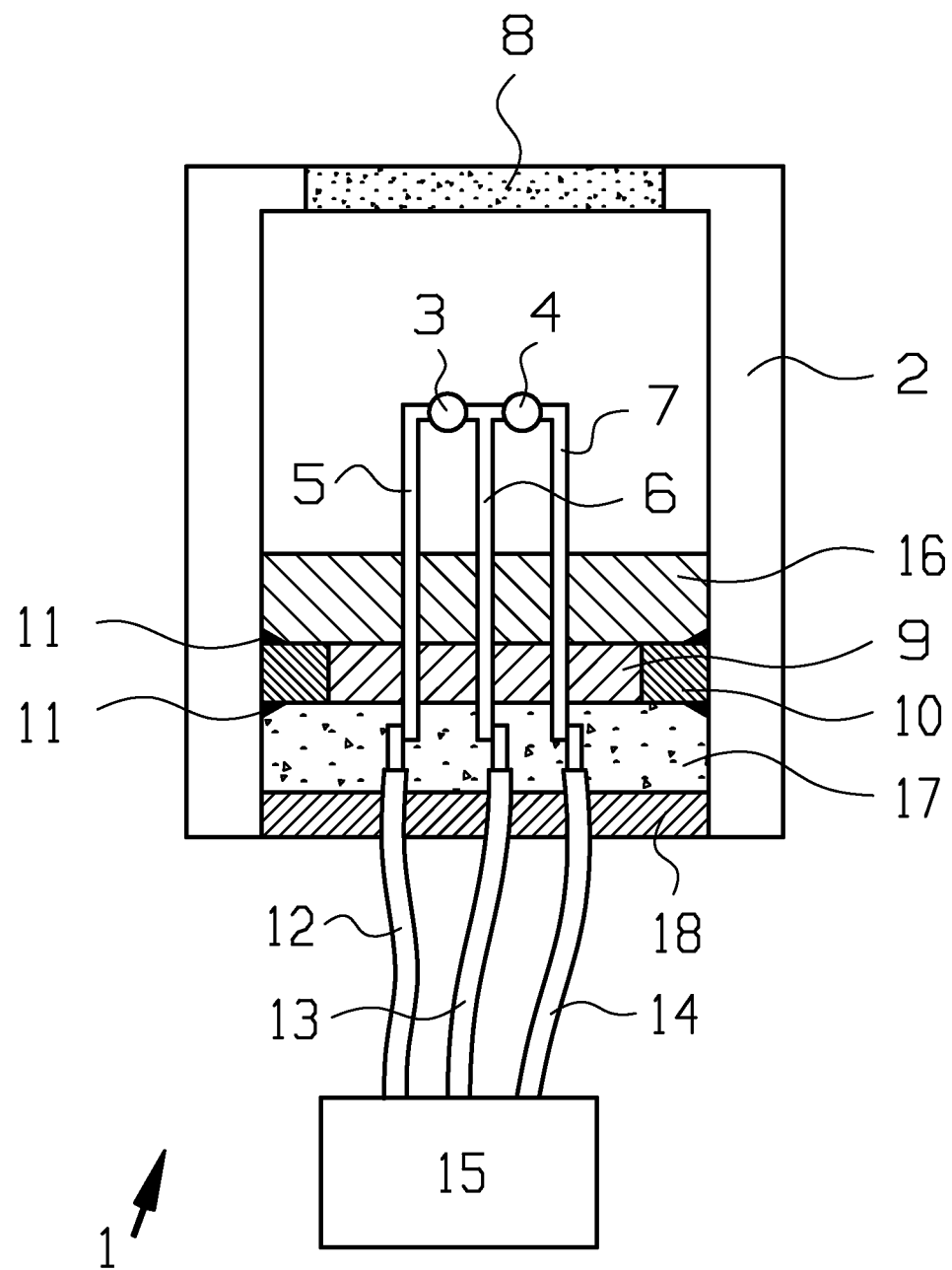
FIG. 1 is a longitudinal sectional view of a gas sensor according to the invention.

Referring to the drawings in particular, a longitudinal section of a gas sensor 1, in which a catalytically active sensor element 3 and a catalytically inactive sensor element 4 are fastened to metal pins 5, 6, 7 in a sensor housing 2. The top side of the sensor housing 2 is closed in the known manner with a porous, gas-permeable portion or gas-permeable pane 8 made of sintered metallic material for the entry of gas. The metal pins 5, 6, 7 are accommodated by a flat glass insert 9, wherein said glass insert 9 is surrounded by a ring-shaped, metallic bottom plate 10, with which a gas-tight connection is established with the sensor housing 2 by means of a weld seam 11. The free ends of the metal pins 5, 6, 7 on the underside of the glass insert 9 are provided with leads 12, 13, 14, which establish the connection with an analyzing unit 15. A casting compound 16, 17 each, consisting of a ceramic mass, with a thickness of 6 mm, is located on the top side and the underside of the glass insert 9. A first casting compound 17 on the underside of the glass insert 9 envelops the contacting of the leads 12, 13, 14 at the metal pins 5, 6, 7, so that electrical insulation of the leads 12, 13, 14, on the one hand, and, on the other hand, pull relief are achieved. A second casting compound 16 is located on the side of the glass insert 9 facing the sensor element 3, 4. In addition, sensor housing 2 is closed on the underside with a casting compound 18 consisting of epoxy resin.

Figure 2:
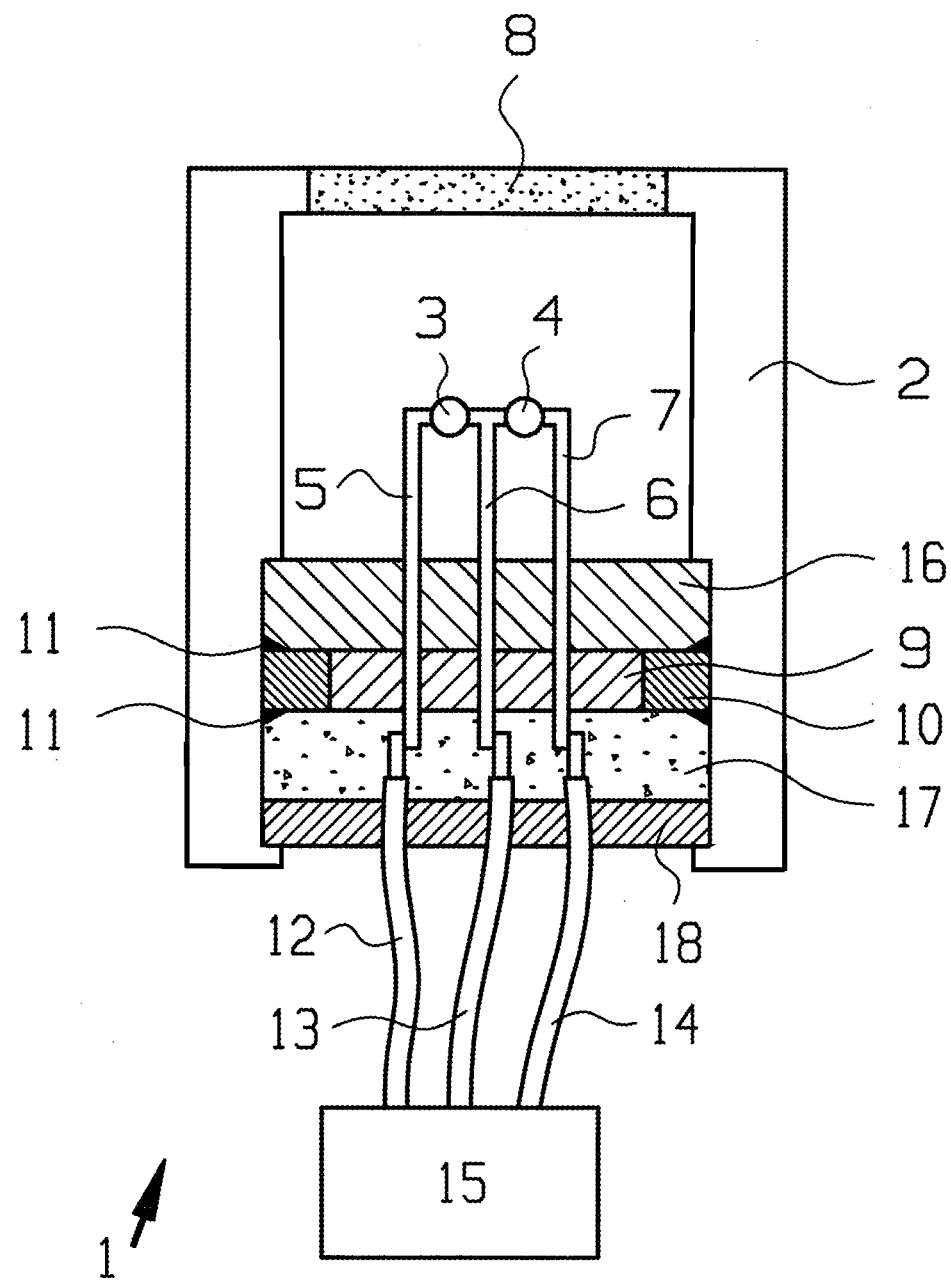
FIG. 2 is a longitudinal sectional view of a gas sensor according to the invention showing the sensor housing provided with an undercut or an internal thread to ensure that the casting compound is in contact with both the glass seal and parts of the sensor housing in a positive-locking manner.

FIG. 2 shows an embodiment that is identical to the embodiment of FIG. 1 except that the sensor housing 2 has a recess respectively receiving casting compounds 16, 17. The recess may be an undercut in the sensor housing 2 as shown or an internal thread to ensure that the casting compound is in contact with both the glass seal and parts of the sensor housing in a positive-locking manner. Each casting compound portion may have its own undercut so that there is a positive-locking connection between the casting compound and the metal housing in the direction of the pressure.

While specific embodiments of the invention have been described in detail to illustrate the application of the principles of the invention, it will be understood that the invention may be embodied otherwise without departing from such principles.

APPENDIX

List of Reference Numbers

1 Gas sensor
2 Sensor housing
3 Active sensor element
4 Inactive sensor element
5, 6, 7 Metal pins
8 Gas-permeable pane
9 Glass insert
10 Bottom plate
11 Weld seam
12, 13, 14 Leads
15 Analyzing unit
16, 17, 18 Casting compound

What is claimed is:
1. An explosion-proof sensor comprising:
one or more metal pins;

a sensor element connected in an electrically conductive manner to said one or more metal pins;

a sensor housing with a gas detection opening closed by a gas permeable portion and with a lead connection opening, the housing defining a gas detection space;

a glass seal forming a sealing surface with said pins passing through said sealing surface for sealing said one or more metal pins, said glass seal comprising a ring-shaped metallic bottom plate and a weld seam providing a gas tight connection of the ring-shaped metallic bottom plate to an interior wall surface of the sensor housing, the ring-shaped metallic bottom plate surrounding a one-piece glass insert and cooperating with said one-piece glass insert to form the sealing surface, the glass insert consisting of glass through which the one or more metal pins pass, the sealing surface extending fully across the lead connection opening and sealing the gas detection space at the lead connection opening; and a bending-resistant casting compound supporting the glass seal at least on one side thereof with said bending-resistant casting compound extending fully across the sealing surface, said glass seal and said bending-resistant casting compound fully closing said lead connection opening and said sensor housing, with said gas detection opening closed by said gas permeable portion and said glass seal and said bending-resistant casting compound fully closing said lead connection opening, said sensor housing fully enclosing said sensor element on all sides.

2. An explosion-proof sensor in accordance with claim 1, wherein the bending-resistant casting compound supporting the glass seal comprises a first casting compound provided on the sensor outside of the glass seal.

3. An explosion-proof sensor in accordance with claim 2, wherein the bending-resistant casting compound supporting the glass seal further comprises a second casting compound arranged on the sensor inside of the glass seal.

4. An explosion-proof sensor in accordance with claim 3, wherein the bending-resistant casting compound supporting the glass seal comprises casting compound on both an inside and an outside of the glass seal.

5. An explosion-proof sensor in accordance with claim 4, wherein
an undercut is present in the sensor housing in an area of the casting compound, so that there is a positive-locking connection between the casting compound and the sensor housing in a direction of pressure.

6. An explosion-proof sensor in accordance with claim 5, wherein the bending-resistant casting compound comprises one or more of cements, ceramic compounds, epoxy resins or polyurethanes as casting materials.

7. An explosion-proof sensor in accordance with claim 6, wherein the thickness of the bending-resistant casting compound is between 3 mm and 25 mm.

8. An explosion-proof sensor in accordance with claim 7, wherein the modulus of elasticity of the bend-resistant casting compound is in a range of 50 kN/mm$^2$ to 380 N/mm$^2$ for ceramic casting compounds, in a range of 1 N/mm$^2$ to 100 N/mm$^2$ for casting compounds from silicones and polyurethanes and in a range of 1 kN/mm$^2$ to 10 kN/mm$^2$ for epoxy resins.

9. An explosion-proof sensor in accordance with claim 4, wherein:
said bending-resistant casting compound supporting said glass seal and said glass seal are positioned in a sandwich configuration;

said sensor housing defines an undercut including an inward undercut edge and an outward undercut edge; and said sandwich configuration is disposed in the undercut between the inward undercut edge and the outward undercut edge to provide a positive-locking connection between said sandwich configuration and said sensor housing.

10. An explosion-proof sensor in accordance with claim 1, wherein the bending-resistant casting compound consists of a plurality of layers.

11. An explosion-proof sensor in accordance with claim 1, wherein the bend-resistant casting compound is a polyurethane or epoxy resin in an area of current or voltage-carrying elements.

12. An explosion-proof sensor in accordance with claim 1, wherein the sensor measures at least one of combustible or toxic gases or detects smoke.

13. An explosion-proof sensor in accordance with claim 1, wherein a thickness of the glass seal is between 0.5 mm and 6 mm.

14. An explosion-proof sensor in accordance with claim 1, wherein a diameter of the glass seal is between 2 mm and 20 mm.

15. An explosion-proof sensor comprising:
a metal pin;
a sensor element connected to said metal pin in an electrically conductive manner;
a metal sensor housing with a gas detection opening closed by gas permeable sintered metallic material and with a lead connection opening, the housing defining a gas detection space;
a pin support and lead connection closure comprising a glass seal comprising a glass insert consisting of glass with said metal pin passing therethrough and in sealing connection with said metal pin and a ring-shaped metallic bottom plate with an inner peripheral portion fixed to said glass insert and with an outer peripheral edge fixed to said metal sensor housing via a weld seam, said pin support and lead connection closure extending fully across said lead connection opening to fully seal said lead connection opening and to provide a sealed pressure barrier closing said lead connection opening whereby said metal sensor housing and said pin support and lead connection closure form a pressure-proof housing enclosure around said gas detection space and said sensor element is positioned within said pressure-proof housing enclosure; and
a bending-resistant casting compound supporting said glass seal at least on one side of said pin support and lead connection closure.

16. An explosion-proof sensor in accordance with claim 15, wherein the bending-resistant casting compound supporting the glass seal comprises casting compound on both an inside and an outside of the glass seal.

17. An explosion-proof sensor in accordance with claim 16, wherein:
the bending-resistant casting compound supporting the glass seal and the glass seal are positioned in a sandwich configuration;
the sensor housing defines an undercut including an inward undercut edge and an outward undercut edge; and
the sandwich configuration is disposed in the undercut between the inward undercut edge and the outward undercut edge to provide a positive-locking connection between the sandwich configuration and the sensor housing.

18. An explosion-proof sensor in accordance with claim 15, wherein the bending-resistant casting compound comprises one or more of cements, ceramic compounds, epoxy resins and polyurethanes as casting materials.

19. An explosion-proof sensor comprising:
- a sensor housing with a gas detection opening closed by a gas permeable portion and with a lead connection opening, the sensor housing defining a gas detection space;
- a gas sensor element positioned within said sensor housing;
- a metal pin connected to said gas sensor element in an electrically conductive manner;
- a pin support and lead connection closure comprising a glass seal in sealing connection with said metal pin within said housing, said glass seal comprising a ring-shaped metallic bottom plate and a weld seam providing a gas tight connection of the ring-shaped metallic bottom plate to an interior wall surface of the sensor housing, the ring-shaped metallic bottom plate surrounding a one-piece glass insert and cooperating with said one-piece glass insert to form the sealing surface, the glass insert consisting of glass through which the one or more metal pins pass, the sealing surface extending fully across the lead connection opening to seal the gas detection space at the lead connection opening said pin support and lead connection closure cooperating with said sensor housing, closed by said gas permeable portion, to fully enclose said gas sensor element, said pin support and lead connection closure having an outer side surface fully bordered by said sensor housing and having an inner side surface fully bordered by said sensor housing; and
- a bending-resistant casting compound supporting the glass seal and fully in contact with at least one of said inner side surface and said outer side surface of said pin support and lead connection closure, said pin support and lead connection closure and said bending-resistant casting compound fully closing said lead connection opening.

20. An explosion-proof sensor in accordance with claim 19, wherein:
- the sensor housing is formed as a metal housing;
- an undercut defining an inner undercut edge and an outer undercut edge, is present in the metal housing;
- the bending-resistant casting compound supporting the glass seal is fully in contact with each of the inner side surface and the outer side surface of said pin support and lead connection closure; and
- said bending-resistant casting compound and said pin support and lead connection closure are disposed in the undercut between the inner undercut edge and the outer undercut edge, so that there is a positive-locking connection between the casting compound and said pin support and the metal housing.

* * * * *